(12) United States Patent
Black et al.

(10) Patent No.: US 7,776,531 B1
(45) Date of Patent: Aug. 17, 2010

(54) COMPOSITIONS AND METHODS FOR STABILIZING SURFACE BOUND PROBES

(75) Inventors: Fiona E. Black, San Diego, CA (US); Steven M. Barnard, San Diego, CA (US); Nels A. Olson, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 762 days.

(21) Appl. No.: 11/341,115

(22) Filed: Jan. 27, 2006

Related U.S. Application Data

(62) Division of application No. 10/809,214, filed on Mar. 25, 2004, now abandoned.

(51) Int. Cl.
*C12Q 1/68* (2006.01)

(52) U.S. Cl. .......................................................... 435/6

(58) Field of Classification Search .................. 435/7.1, 435/7.2, 7.91, 7.92; 436/516, 518
See application file for complete search history.

(56) References Cited

U.S. PATENT DOCUMENTS

| | | | |
|---|---|---|---|
| 3,929,741 A | 12/1975 | Laskey | |
| 4,080,476 A | 3/1978 | Laskey | |
| 4,868,130 A | 9/1989 | Hargreaves | |
| 5,004,685 A | 4/1991 | Arai et al. | |
| 5,492,837 A | 2/1996 | Naser-Kolahzadeh et al. | |
| 6,051,388 A | 4/2000 | Bodenhamer | |
| 6,251,691 B1 | 6/2001 | Seul | |
| 6,327,410 B1 | 12/2001 | Walt et al. | |
| 6,485,690 B1 | 11/2002 | Pfost et al. | |
| 6,589,779 B1 | 7/2003 | McDevitt et al. | |
| 6,716,629 B2 | 4/2004 | Hess et al. | |
| 2002/0095073 A1 | 7/2002 | Jacobs et al. | |
| 2003/0224506 A1 | 12/2003 | Agrawal et al. | |

OTHER PUBLICATIONS

Rehman et al. (Nucleic Acid Research 1999 vol. 27, p. 649-655).*
DyeSaver Anti-fade coating Protocol, May 3, 2004, [online], [retrieved on Jul. 19, 2004] Retrieved from the Genisphere website <URL: www.genisphere.com/array_detection_protocols.html>.
DyeSaver2 Protocol, Mar. 29, 2004, [online], [retrieved on Jul. 19, 2004] Retrieved from the Genisphere website <URL: www.genisphere.com/array_detection_protocols.html>.
Flounders, A.W. et al., "Immobilization, stabilization and patterning techniques for enzyme based sensor systems," Proc. of SPIE, 2978: 58-61 (1997).

* cited by examiner

*Primary Examiner*—Jacob Cheu

(57) ABSTRACT

The present invention provides a method for detecting a target analyte by providing a substrate having attached polynucleotides and a stabilization polymer layer; removing the stabilization polymer layer; contacting the substrate with a target analyte; and detecting the target analyte.

24 Claims, 3 Drawing Sheets

US 7,776,531 B1

COMPOSITIONS AND METHODS FOR STABILIZING SURFACE BOUND PROBES

This application is a divisional of U.S. patent application Ser. No. 10/809,214, filed Mar. 25, 2004, now abandoned which is incorporated herein by reference.

This invention was made with government support under grant number CA83398 awarded by the United States National Institute of Health. The United States Government has certain rights in this invention.

BACKGROUND OF THE INVENTION

This invention relates generally to analytical detection of target molecules with probe molecules, and more specifically to extending the shelf life and stability of analytical probes under ambient or packaged conditions.

Biological systems, and in particular biomolecules from these systems, have a remarkable ability to recognize specific target analytes within complex mixtures. This specificity has been exploited for the manufacture of analytical devices having biomolecule probes that allow detection of target analytes in a variety of test samples. Specific analytes can be individually detected in samples that are very complex with respect to the presence of contaminants or other analytes including, for example, synthetic reaction mixtures, environmental samples, or tissue or fluid samples obtained from individuals. Microarray technology uses analytical detection devices having thousands of biomolecules for the simultaneous analysis of entire ensembles of target analytes in complex systems. Microarray technology using nucleotide probes is routinely used for a variety of important applications including, for example, genome-wide quantitative analysis of gene expression and large-scale single nucleotide polymorphism (SNP) discovery and genotyping.

Microarrays are also beginning to play a role in the reinvention of cancer classification and drug discovery. Importantly, microarray technology has allowed investigators to progress from studying the expression of one gene in several days to hundreds of thousands of genes simultaneously in a matter of hours. Since cancer is a product of aberrant expression for large sets of genes, microarray technology is revolutionizing cancer diagnosis. Accordingly, large sets of genes, whose patterns of expression detect the presence of cancer, identify tumor type or characterize a unique property of a tumor, can be evaluated to determine a diagnosis or prognosis of a cancer patient. For example, gene expression profiling using microarrays has been demonstrated to distinguish tumor type and provide insight on clinical outcome for several cancers including lymphomas and leukemias.

Microarray technology is also useful for monitoring gene expression in premalignant and tumorigenic cells following exposure to anticancer agents. Thus, in a research setting microarray technology can be used in conjunction with known anticancer agents to identify better, specific markers for cancer diagnosis, prognosis and treatment. Microarray technology can also be used in a research setting to evaluate candidate anticancer drugs. For example, the effect that a candidate anticancer agent has on gene expression patterns in a cancerous cell can be used to determine the mechanism of action of pharmaceutical agents or potential adverse outcomes for the development of safer and more efficacious drugs. Similar analytical procedures can also be carried out in a clinical setting with biopsies from cancer patients in order to predict onset of unwanted side effects or other adverse events before they occur to the detriment of the patient.

Microarray technology can also be used to monitor environmental exposure to chemicals in humans. Again, because exposure to pathogens or hazardous chemicals causes global changes in gene expression, alterations in microarray expression profiles can be used to determine the nature and level of exposure to hazardous chemicals. Monitoring exposure to chemicals and pathogens can be useful in a variety of settings including, for example, occupational health such as manufacturing facilities in which there is a risk of exposure to chemicals used in the manufacturing process, security checkpoints such as airports or government buildings or battle zones such as those in which combatants may be exposed to biological warfare agents or chemical warfare agents.

Microarrays and other analytical devices that rely on biomolecule probes, and other sensitive probes, are susceptible to degradation in several conditions of storage, transportation and use. Such degradation can lead to a reduction in sensitivity or even an increase in the risk of incorrect diagnosis due to artifacts. Although it is possible to avoid degradation in some cases by minimizing contact of a microarray to such conditions, many applications that would otherwise benefit from use of a microarray are precluded. For example, inability of microarrays to survive storage and transportation conditions post manufacturing can compromise or even preclude their use in some field, laboratory or clinic locations.

Thus, there exists a need for methods of increasing the stability of probe arrays under typical conditions of storage and/or use. The present invention satisfies this need and provides other advantages as well.

BRIEF SUMMARY OF THE INVENTION

The present invention provides a probe composition, including (a) a substrate; (b) a probe molecule attached to the substrate; and (c) a stabilization polymer layer on the substrate, wherein said stabilization polymer layer coats the probe molecule.

The invention further provides a method of making a probe composition. The method includes the steps of (a) providing a substrate having an attached biopolymer probe; and (b) contacting the substrate with a stabilization polymer.

Also provided is a method of shipping a solid-phase probe. The method includes the steps of (a) providing a substrate having an attached probe molecule, and further having a stabilization polymer layer; (b) placing the substrate in a package; and (c) shipping the package to a remote location.

DETAILED DESCRIPTION OF THE INVENTION

Figure 1:
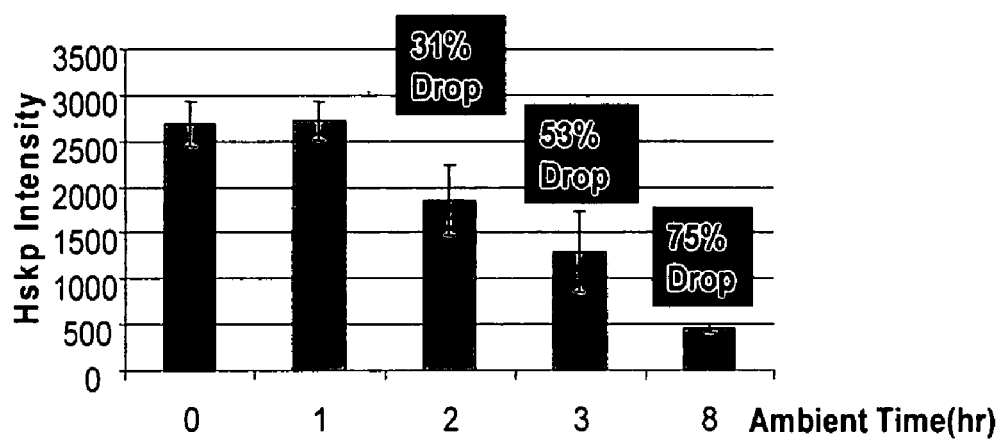
FIG. 1 shows signal intensity in response to exposure of arrays to ambient conditions for 2, 3 and 8 hours, respectively when expression of housekeeping genes was measured.

This invention provides surface bound probe molecule that are stabilized by the presence of a stabilization polymer layer. In particular, the stabilization polymer layer inhibits degradation of probe molecules such that the half life of probe molecules in the presence of the stabilization polymer layer is greater than in the absence of the stabilization polymer layer. Also provided are methods for making a surface bound probe molecule having a stabilization polymer layer. An advantage of the compositions and methods disclosed herein is that, compared to surface bound probe molecules lacking a stabilization polymer layer, they can increase the shelf life of a surface bound probe molecule during storage or transportation, increase stability of a surface bound probe molecule during assay of a target analyte sample or increase the number of times a surface bound probe molecule can be reused with different target analyte samples. Accordingly, this disclosure provides methods for storing a surface bound probe molecule, transporting a surface bound probe molecule and reusing a surface bound probe molecule to detect target analytes in different samples.

In the following description, for the purposes of explanation, specific details are set forth in order to provide a thorough understanding of the present invention. Those skilled in the art will understand that the present invention can be practiced without these specific details and can be applied to any of a variety of related systems. For example, although the methods are described in the context of biopolymer probes, it is understood that the methods can be applied to other types of molecular probes including, for example, synthetic molecules such as those present in a combinatorial library, synthetic polymers, non-polymeric synthetic molecules, non-polymeric biomolecules, naturally occurring molecules, or a mixture including one or more of these types of molecular probes with or without biopolymer probes. Similar molecules can also be used as target analytes in the invention.

Definitions

As used herein, the term "polymer" is intended to mean a molecule having several monomer units covalently attached in a repeating structure. The term is intended to be consistent with its use in the art and, therefore, can include molecules in which each monomer unit is identical, such as polyacrylamide which typically contains identical acrylamide monomer units, or those in which the repeating structure includes only a portion of the monomer, such as polypeptides which have a repeating peptide backbone and differing amino acid side groups or polynucleotides which have a repeating sugar-phosphate backbone and different bases attached thereto. A useful polymer can have two or more monomer subunits including, for example, at least 3, 5, 10, 15, 20, 25, 30, 40 or 50 monomer subunits. A polymer can also be characterized according to molecular weight being, for example, at least 5, 10, 15, 20, 25, 30, 40, 50, 100, $1 \times 10^3$, $5 \times 10^3$, $1 \times 10^4$, $5 \times 10^4$, $1 \times 10^5$, $5 \times 10^5$, $1 \times 10^6$ or $5 \times 10^6$ kiloDaltons. Those skilled in the art will understand that a population of polymers can be characterized with respect to the average molecular weight or average length of the polymers in the population.

As used herein, the term "non-naturally occurring" when used in reference to a molecule means that the molecule is not typically synthesized by a living organism in its native environment.

As used herein, the term "biopolymer" is intended to mean a polymer that is capable of being synthesized by a living organism or an analog of such a polymer. Exemplary biopolymers include, without limitation, polypeptides, polynucleotides and polysaccharides. Useful biopolymer analogs include molecules that have structure similar to the biopolymer or mimetics having a similar activity such as ability to bind specifically to a particular binding partner of the biopolymer. A biopolymer can be used as a probe or target analyte in the methods and compositions set forth herein.

A polynucleotide useful in the present invention will generally contain phosphodiester bonds, and can include, for example, DNA or RNA. If desired to suit a particular application, polynucleotide analogs having alternate backbones can be used, including, for example, phosphoramide (Beaucage et al., *Tetrahedron* 49(10): 1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphosphoroamidite linkages (see Eckstein, *Oligonucleotides and Analogues: A Practical Approach*, Oxford University Press), or peptide nucleic acid linkages (see Egholm, *J. Am. Chem. Soc.* 114:1895 (1992); Meier et al., *Chem. Int. Ed. Engl.* 31:1008 (1992); Nielsen, *Nature,* 365:566 (1993); Carlsson et al., *Nature* 380:207 (1996), all of which are incorporated by reference). Other polynucleotide analogs include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, *ASC Symposium Series* 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, *ASC Symposium Series* 580, "Carbohydrate Modifications in Antisense Research", Ed. Y. S. Sanghui and P. Dan Cook. polynucleotides containing one or more carbocyclic sugars can also be used in the invention (see Jenkins et al., *Chem. Soc. Rev.* (1995) pp 169-176). Several nucleic acid analogs are described in Rawls, C & E News Jun. 2, 1997 page 35. All of these references are hereby expressly incorporated by reference. If desired, these modifications of the ribose-phosphate backbone can be included in a polynucleotide to facilitate the addition of labels, or to increase the stability and half-life of such molecules in physiological environments.

As will be appreciated by those in the art, mixtures of one or more of the biopolymers set forth above can be used in the invention including, for example, a mixture including a naturally occurring polynucleotide and a polynucleotide analog. In particular embodiments, mixtures of different polynucleotide analogs, and mixtures of naturally occurring polynucleotides and analogs thereof can be made and used.

A polynucleotide can be single stranded, double stranded or contain portions of both double stranded and single stranded sequence. A polynucleotide can be DNA, such as genomic DNA (gDNA) or copy DNA (cDNA); RNA such as messenger RNA (mRNA), transfer RNA (tRNA), ribosomal RNA (rRNA), antisense RNA (aRNA) or RNA inhibitor (RNAi); or a hybrid, where the polynucleotide contains any combination of deoxyribo- and ribo-nucleotides, and any combination of bases, including uracil, adenine, thymine, cytosine, guanine, inosine, xanthanine, hypoxathanine, isocytosine, isoguanine, or the like. Particular embodiments utilize isocytosine and isoguanine as is generally described in U.S. Pat. No. 5,681,702.

Also useful in the methods and compositions described herein are nucleosides. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid, each containing a base, are referred to herein as a nucleoside.

A polypeptide useful in the methods and compositions described herein can have naturally occurring amino acids and peptide bonds, or synthetic peptidomimetic structures. The side chains may be in either the (R) or the (S) configuration. In a particular embodiment, the amino acids are in the (S) or L-configuration. If non-naturally occurring side chains are used, non-amino acid substituents may be used. Exemplary polypeptides that can be made and used include, without limitation, an antigen, immunoglobulin, antibody, enzyme, ligand binding receptor, T-cell receptor, kinase, phosphatase, lectin, G-protein coupled receptor, or functional fragments thereof. The functional fragments having, for example, binding specificity for a ligand of the full length polypeptide.

As used herein, the term "stabilization polymer layer" is intended to mean a population of polymer molecules that contact a solid-phase probe molecule and inhibit degradation of the probe molecule. A stabilization polymer layer can inhibit degradation that would otherwise reduce signal from the probe molecule due to the presence of a target analyte. A stabilization polymer layer is typically a continuous film. A stabilization polymer layer can have one or more interruption in a uniform or non-uniform fashion, so long as it is still capable of inhibiting degradation of a probe molecule. For example, a stabilization polymer layer can contact the substrate portion or probe molecule portion of a solid-phase probe molecule or both portions. A stabilization polymer layer can cover all or portion of a substrate, substrate bound probe molecule or both. Inhibition of degradation of a molecule includes, for example, reducing or preventing detachment of the molecule from a solid support, reducing or preventing covalent modification of the molecule, reducing or preventing chemical oxidation of the molecule, reducing or preventing chemical reduction of the molecule, or reducing or preventing irreversible changes to the molecule structure or conformation. A stabilization polymer can be a linear polymer, an interpolymer containing crosslinked linear polymers, a branched polymer or a dendrimeric polymer.

As used herein, the term "shipping" is intended to mean causing to be transported. An item can be caused to be transported, for example, by providing the item to a courier or postal service. In some embodiments, an item can be caused to be transported from a first location to a second location, including, for example, a second location that is proximal or in a remote location. Exemplary remote locations include those in separate cities or separate countries. The item can be shipped with or without packaging as set forth in further detail below.

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Further examples of arrays that can be used in the invention include, without limitation, those described in Butte, *Nature Reviews Drug Discov.* 1:951-60 (2002) or U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

An exemplary high density array that can be used is an array of arrays or a composite array having a plurality of individual arrays that is configured to allow processing of multiple samples. Such arrays allow multiplex detection of large pluralities of target loci and/or interrogation of large populations of probes. Exemplary composite arrays that can be used in the invention are described in U.S. Pat. No. 6,429,027 and U.S. Pat. App. Pub. No. 2002/0102578. In particular embodiments, each individual array can be present within each well of a microtiter plate by attachment to the well or temporary introduction to the well. Thus, depending on the size of the microtiter plate and the size of the individual array, very high numbers of assays can be run simultaneously; for example, using individual arrays of 2,000 probes and a 96 well microtiter plate, 192,000 assays can be performed in parallel; the same number of probes in each well of a 384 microtiter plate yields 768,000 simultaneous assays, and in a 1536 microtiter plate gives 3,072,000 assays.

As used herein, the term "substrate" is intended to mean a material having a rigid or semi-rigid surface. A substrate can have a surface that repels water or is resistant to absorbing water. Alternatively, a substrate can be water absorbent, so long as the structural integrity of the substrate is not adversely affected by the presence of a stabilization polymer layer. Exemplary materials that can be used as a substrate include, but are not limited to, glass; modified or functionalized glass; plastic such as acrylic, polystyrene or a copolymer of styrene and another material, polypropylene, polyethylene, polybutylene, polyurethane or Teflon; polysaccharides or crosslinked polysaccharides such as agarose or Sepharose; nylon; nitrocellulose; resin; silica or silica-based materials including silicon and modified silicon; carbon-fiber; metal; inorganic glass; optical fiber bundle, or a variety of other polymers. A substrate can be a particle such as a microsphere or bead. Exemplary particles include, without limitation, controlled pore glass beads, paramagnetic beads, thoria sol, Sepharose beads, nanocrystals and others know in the art as described, for example, in *Microsphere Detection Guide* from Bangs Laboratories, Fishers Ind. A substrate can also have a planar surface to which different probes are attached such as a microscope slide or well of a multiwell plate.

As used herein, the term "specifically bind" is intended to mean preferential binding of one partner to another compared to binding of the partner to other components or contaminants in the system. Binding partners that are specifically bound typically remain bound under the detection or separation conditions described herein, including wash steps to remove non-specific binding. Depending upon the particular binding conditions used, the dissociation constants of the pair can be, for example, less than about $10^{-4}$, $10^{-5}$, $10^{-6}$, $10^{-7}$, $10^{-8}$, $10^{-9}$ $10^{-10}$, $10^{-11}$, or $10^{-12}$ $M^{-1}$. Polynucleotides can specifically bind to each other when they have substantially complementary sequences. The relationship of probe complementary and stringency of hybridization sufficient to achieve specificity is well known in the art as described, for example, in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998). Two polynucleotides can be, for example, perfectly complementary or can contain from 1 to many mismatches so long as the hybridization conditions are sufficient to allow probe discrimination between a target sequence and a non-target sequence. Accordingly, substantially complementary polynucleotides can contain sequences that are 100% complementary or that have lesser degrees of complementarity including, for example, at least about 75, 80, 85, 90, 91, 92, 93, 94, 95, 96, 97, 98 or 99% complementary.

Description of Particular Embodiments

The present invention provides a probe composition, including (a) a substrate; (b) a probe molecule attached to the substrate; and (c) a stabilization polymer layer on the substrate, wherein said stabilization polymer layer coats the probe molecule.

A stabilization polymer layer can include any polymer capable of coating a probe molecule and maintaining activity of the probe in detecting its target. Exemplary stabilization polymers include, without limitation, non-naturally occurring polymers such as polyacrylamide, polyvinylpyrrolidine, polymethylacrylate, or polyethylene glycol or derivatives thereof. Examples of useful derivatives are polyhydroxyethylmethacrylate and polybutylacrylamide-co-acrylamide. Copolymers are also useful such as glycol polymethacrylate. If desired, any of the above-identified synthetic polymers can be specifically excluded from a stabilization polymer layer.

A stabilization polymer useful in the invention can be a naturally occurring polymer including, but not limited to, hyaluronic acid (poly d-glucuronic acid-n-acetyl-d-glucosamine), cellulose, chitin, starch, gelatin, or agarose. Others include the carrageenans which are a naturally occurring family of polysaccharides derived from red seaweed with names such as Gelcarin, Viscarin and SeaSpen PF (FMC Corp., Philadelphia, Pa.). Other useful stabilization polymers include derivatives of naturally occurring polymers including, for example, Klucel® (hydroxypropylcellulose). If desired, any of the above-identified natural polymers or derivatives thereof can be specifically excluded from a stabilization polymer layer.

Typically, a stabilization polymer is inert to binding with or modifying a probe molecule, target analyte or both. A stabilization polymer can further provide a function of blocking non-specific binding of analytes to a substrate that is attached to a probe molecule. However, in an alternate embodiment, a stabilization polymer useful in the invention can be substantially incapable of blocking non-specific binding of one or more analytes in a test sample to a substrate attached to a probe. A molecule that is substantially incapable of blocking non-specific binding when present will have a negligible effect on non-specific binding when compared to absence of the molecule. In particular embodiments, a stabilization polymer can exclude bovine serum albumin, casein, milk protein, detergents and other agents typically used to prevent non-specific binding in solid-phase assays.

In a particular embodiment a stabilization polymer is a different type of molecule than the probe molecule type. For example, in embodiments where a polynucleotide probe or target is used, it will typically be desirable to use a non-polynucleotide stabilization polymer, thereby preventing binding of the stabilization polymer to the probes or their targets. Thus, a stabilization polymer can be a non-polypeptide polymer when polypeptide probes or targets are used. However, if desired the stabilization polymer can be a similar type of molecule as the probe molecule. Taking again the example of a polynucleotide probe, a polynucleotide stabilization layer can be used so long as the sequence of the polynucleotide in the stabilization layer differs from the probe or target such that the stabilization layer does not prevent detection of the target by the probe. Alternatively, unwanted interactions between a stabilization polymer and substrate-attached probe molecule or target analyte can be prevented by removing the stabilization polymer from the substrate prior to contacting the probe molecule with the target analyte.

A stabilization polymer can have one or more of several properties including, for example, ability to inhibit degradation of a probe molecule, ability to limit conformational freedom of a probe molecule, ability to retain water, ability to remain optically transparent in a particular radiation wavelength range. Thus, a useful stabilization polymer can have oxygen radical scavenging properties or ability to limit access of a probe molecule to ambient oxygen radicals. Stabilization polymers that are capable of retaining at least 2%, 10%, 50%, 75%, or 100% weight of water (compared to dry weight of the polymer, "w/w") are useful. Also useful are polymers that retain large excesses of water including, for example, at least 2, 5 or 10 fold excess water w/w. Optical transparency is typically desired in the visible, ultraviolet and/or infrared region of the spectrum. However, transparency outside of this region is also useful in some applications of the invention as is transparency in particular regions of the visible spectrum such as one or more of the red, orange, yellow, green, or blue regions. Stabilization polymer layers lacking one or more of the above properties can also be used in the invention, if desired.

In embodiments wherein a stabilization polymer layer lacks a particular property it is possible to combine the stabilization polymer with one or more agents that have the property. For example, a stabilization polymer layer useful in the invention can be substantially incapable of oxygen scavenging activity. In such embodiments, the layer coating a solid-phase probe can include an oxygen scavenger such as propyl gallate or derivatives of methoxycinnamate such as ethylhexyl methoxycinnamate. Other agents that can be added to a stabilization polymer layer include, for example, trehalose and vinyl pyrrolidone.

A stabilization polymer is typically polymerized prior to being contacted with a substrate to which a probe is to be attached or substrate-bound probe. It is contemplated that monomers can be contacted with a substrate either in the presence or absence of an attached probe molecule and the monomers polymerized to form a stabilization polymer layer.

Any of a variety of probe molecules can be used in a method or composition of the invention including, for example, a biopolymer probe. A biopolymer probe useful in the invention can include any biopolymer capable of being attached to a substrate such that it can specifically interact with a target analyte to indicate the presence of the target analyte in a test sample. Exemplary interactions that can indicate presence of a target analyte include, but are not limited to, binding between a biopolymer probe and target analyte to form a detectable complex; modification of a biopolymer probe by a target analyte to incorporate, remove or alter a detectable property of the biopolymer probe; modification of a target analyte by a biopolymer probe to incorporate, remove or alter a detectable property of the target analyte; or modification of the environment of the biopolymer probe or target analyte to incorporate, remove or alter a detectable property of the environment. As set forth above, a stabilization polymer layer is typically selected to allow such interactions or can be removed prior to contacting probe molecules with target analytes.

In particular embodiments, a biopolymer probe of the invention is a polynucleotide. A polynucleotide probe useful in the invention can have any of a variety of compositions or sizes, so long as it has the ability to specifically bind to a target analyte such as a target polynucleotide or polypeptide. A polynucleotide probe can be a molecule having a native nucleic acid structure or an analog thereof. Exemplary polynucleotide probes that can be used in a method of the invention include, without limitation, those set forth above in the definitions.

A polynucleotide probe can be used to detect the presence of a particular target sequence in a test sample. Accordingly a polynucleotide probe can have a sequence that is complementary to a locus or other sequence feature in a target polynucleotide. This complementarity need not be perfect. For example, there can be any number of base pair mismatches between a polynucleotide probe and target polynucleotide, so long as the mismatches do not prevent formation of a sufficiently stable hybridization complex for detection under the conditions being used.

Furthermore, a polynucleotide probe can have a sequence or sequence region that is not complementary to a target sequences or other sequences present in a particular polynucleotide sample. These non-target complementing sequence regions can include, for example, a linker sequence for attaching a probe to a substrate, annealing site for another polynucleotide such as a primer, an identifier sequence used for encoding or decoding the location of probes on an array or other desired sequences. A polynucleotide probe can have a capture sequence that hybridizes to an artificial address sequence. Thus, a polynucleotide probe can be part of a universal array as set forth below.

A target-complementing sequence region of a polynucleotide probe can have a length that is, for example, at least 10 nucleotides in length. Longer target-complementing regions can also be useful including, without limitation, those that are at least about 15, 20, 25, 35, 50, 70, 100, 500, 1000, or 5000 nucleotides in length or longer. In particular embodiments, such as detection of small target sequences, a target-complementary region of a polynucleotide probe can be at most about 100, 90, 80, 70, 60, 50, 40, 35, 30, 25, 20, or 10 nucleotides in length.

In particular embodiments, a biopolymer probe of the invention is a polypeptide. A polypeptide probe useful in the invention can have any of a variety of compositions or sizes, so long as it has the ability to specifically bind to a target analyte such as a target polynucleotide or polypeptide. A polypeptide probe can be a molecule having a native structure or an analog thereof. Exemplary polypeptide probes that can be used in a method of the invention include, without limitation, those set forth above in the definitions.

A polypeptide probe can have a length that is, for example, at least 10 amino acids in length. Longer polypeptides can also be useful including, without limitation, those that are at least about 15, 20, 25, 50, 100, 1000, 5000 or 10,000 amino acids in length or longer. Furthermore, a polypeptide probes can have a multimeric structure such as occurs in antibodies which have 4 separate polypeptide strands. In particular embodiments, a polypeptide probe can have more than one polypeptide strand associated together including, for example, at least 2, 3, 4, 5 or more separate polypeptide strands.

A probe molecule used in a method of the invention can further have a modification, for example, to allow attachment to a substrate or to support a particular detection method. In particular embodiments, a probe can include a detectable label including, without limitation, one or more of the primary or secondary labels set forth below. Alternatively, a probe molecule can lack extrinsic labels, for example, in embodiments wherein detection is based on an intrinsic characteristic of the probe. Examples of intrinsic characteristics that can be detected include, but are not limited to, mass, electrical conductivity, energy absorbance, fluorescence, optical rotation or the like. Typically, an intrinsic or extrinsic label that is used in a method or composition set forth herein will be detectable in the presence of a stabilization polymer layer. Thus, a stabilization polymer layer can be undetectable under the conditions used to detect an intrinsic or extrinsic label in a method of the invention.

A probe molecule can be attached to a substrate by a covalent linkage or other linkage that is sufficiently stable to allow detection of a target analyte under a desired set of conditions. Any of a variety of well known coupling chemistries can be used to covalently attach a probe molecule to a substrate. Those skilled in the art will know or be able to determine appropriate linkage chemistry for a particular type of molecule to be attached to the substrate. Exemplary linkage chemistries useful in the invention are described, for example, in US Application Publication No. 2002/0102578 and Hermanson, *Bioconjugate Techniques*, Academic Press, San Diego (1996). Typically, a stabilization polymer layer is added to a substrate following attachment of one or more probes. However, if desired a stabilization polymer layer can be added prior to or during a probe attachment procedure, so long as the stabilization polymer layer is compatible with the conditions used for probe attachment.

In some embodiments, biopolymer probes such as polynucleotides or polypeptides can be attached to a substrate by sequential addition of monomer units directly on a solid support. Methods known in the art for synthesis of a variety of different chemical compounds on solid supports can be used, such as methods for solid phase synthesis of peptides, organic moieties, and nucleic acids. Alternatively probe molecules can be synthesized first, and then attached to a solid support. Probes can be attached covalently, for example, via reaction with functional groups on a solid support. Functionalized solid supports can be produced by methods known in the art and, if desired, obtained from any of several commercial suppliers for beads and other supports having surface chemistries that facilitate the attachment of a desired functionality by a user. Exemplary surface chemistries that are useful in the invention include, but are not limited to, amino groups such as aliphatic and aromatic amines, carboxylic acids, aldehydes, amides, chloromethyl groups, hydrazide, hydroxyl groups, thiols, sulfonates or sulfates. Accordingly, a probe molecule can be attached to a solid support via a chemical linker. Such a linker can have characteristics that provide, for example, stable attachment, reversible attachment, sufficient flexibility to allow desired interaction with a target analyte, or prevention of undesirable binding interactions. Further exemplary methods that can be used in the invention to attach probe molecules to a solid support are described in Pease et al., *Proc. Natl. Acad. Sci. USA* 91(11):5022-5026 (1994); Khrapko et al., *Mol Biol (Mosk)* (USSR) 25:718-730 (1991); Stimpson et al., *Proc. Nail. Acad. Sci. USA* 92:6379-6383 (1995) or Guo et al., *Nucleic Acids Res.* 22:5456-5465 (1994).

A probe molecule, such as the biopolymer probes described previously herein, can be attached to a substrate by non-covalent association. For example, a probe molecule can be attached to a substrate via association of a pair of binding partners, one being present on the probe molecule and the other being present on the substrate. Exemplary binding partners that can be used include, without limitation, avidin and biotin, complementary nucleic acid sequences, a receptor and ligand, antibody and epitope, chelating moiety and metal, or lectin and polysaccharide. Binding partners can be moieties that are intrinsic to a probe molecule, substrate or both. For example, a polynucleotide probe having a negatively charged backbone structure can be associated with a positively charged surface. Alternatively, extrinsic binding partners can be moieties added to a probe molecule, substrate or both. For example, a substrate can be modified to have an avidin or streptavidin moiety bound to its surface and a probe molecule can have an attached biotin moiety such that association of the avidin or streptavidin moiety with the biotin attaches the probe molecule to the substrate surface. Those skilled in the art will know or be able to determine appropriate binding partner moieties that are compatible with the particular substrate, probe molecule, stabilization polymer and other components used in a composition or method set forth herein.

A substrate used in the invention can be made from any material that can attach to a desired molecule probe and that is capable of supporting a stabilization polymer layer. Useful substrate materials include, but are not limited to, glass; modified glass; functionalized glass; plastic such as acrylic, polystyrene and copolymer of styrene and another material, polypropylene, polyethylene, polybutylene, polyurethane, Teflon, or the like; polysaccharide; nylon; nitrocellulose; resin; silica; silica-based material such as silicon or modified silicon; carbon; metal; inorganic glass; optical fiber, or any of a variety of other polymers. Useful substrates include, but are not limited to, those that allow optical detection, for example, by being translucent to energy of a desired detection wavelength and/or do not themselves appreciably fluoresce in a desired detection wavelength.

A substrate can be selected based on one or more properties that facilitate supporting a stabilization polymer layer. For example, properties of the substrate such as surface charge, surface topology or availability of hydrogen bonding groups, hydrophobicity or hydrophilicity can be selected for compatibility with a particular stabilization polymer. In particular embodiments, a hydrophilic substrate can be used with a polar or hydrophilic stabilization polymer; a hydrophobic substrate can be used with a hydrophobic or nonpolar stabilization polymer layer; a hydrophilic substrate can be used with a nonpolar or hydrophobic stabilization polymer; a hydrophobic substrate can be used with a hydrophilic or polar stabilization polymer layer; a charged substrate can be used with a stabilization polymer layer having opposite charge; or a substrate having hydrogen bonding groups can be used with a stabilization polymer layer that is capable of forming hydrogen bonds. Those skilled in the art will know or be able to determine appropriate combinations of polymer and substrate layer that are compatible with the use of the probes on the substrate including, for example, combinations that do not result in an adverse amount of nonspecific binding of components in a target sample. Those skilled in the art will know or be able to determine compatible properties of a substrate and a stabilization polymer layer. Furthermore, if desired a substrate can be coated with an agent that enhances interaction with a particular stabilization polymer layer such as a block copolymer. For example, a charged surface of a substrate can be masked to allow favorable interaction with a hydrophobic stabilization polymer layer, for example, by applying a substance having a charged portion that will interact with the substrate and a hydrophobic portion that will interact with the stabilization polymer.

A substrate useful in the invention can have any of a variety of shapes to suit particular applications, so long as the substrate is capable of attaching a probe molecule and supporting a stabilization polymer layer. Exemplary shapes include, without limitation, a substantially flat surface, planar surface, surface having raised features such as barriers, surface having indented features such as wells or channels, or a particle having a rigid surface such as a microsphere, bead, disk, plate, chip, sliver or irregular shape. Particle sizes can range, for example, from nanometers such as about 100 nm beads, to millimeters, such as about 1 mm beads, with particles of intermediate size such as at most about 0.2 micron, 0.5 micron, 5 micron or 200 microns being useful. In addition, particles used in the invention can be porous, thus increasing the surface area available for attachment of probe molecules and detection of target analytes. Pore size can be any that is large enough to accommodate the particular probe molecules to be attached or target analytes to be detected. In cases where probe molecules are attached within the pores of a particular substrate, a stabilization polymer can have a molecular weight that is sufficiently small to form a layer within the pores. Alternatively, a stabilization layer can be formed external to the pores in which case larger molecular weight stabilization polymers can be selected. Those skilled in the art will know or be able to determine an appropriate molecular weight of a polymer to allow entry to a porous substrate using, for example, estimations germane to size exclusion chromatography methods.

In particular embodiments, a controlled pore glass (CPG) particle can be used. CPG having any of a variety of particle sizes and pore sizes can be used in the invention including, for example, CPG with a median particle size falling within about 37 to 177 microns and a median pore size falling within about 65 to 3300 Angstroms. A particularly useful CPG has a median particle size and pore size of about 100 microns and about 1400 Angstroms, respectively. Those skilled in the art will recognize that CPG and other particles are typically obtained with a median particle size specification and there can be variation within a lot. For example, a lot of 100-micron CPG can include members as small as about 75 or as large as about 125 microns. It will be understood that the above described ranges, as with all ranges described herein, are intended to include individual integer and non integer values therein.

Particle material can vary depending, for example, on the method of attaching probe molecules, method of detecting target analytes or the type of stabilization polymer used. Suitable materials include, but are not limited to, those used in peptide, nucleic acid and organic moiety synthesis, such as plastics, ceramics, glass, polystyrene, methylstyrene, acrylic polymers, paramagnetic materials, thoria sol, carbon graphite, titanium dioxide, latex or cross-linked dextrans such as Sepharose™, cellulose, nylon, cross-linked micelles or Teflon™. Useful particles are described, for example, in *Microsphere Detection Guide* from Bangs Laboratories, Fishers Ind.

In particular embodiments, a plurality of different probe molecules can be attached to a substrate or otherwise spatially distinguished in an array. Exemplary arrays that can be used in the invention include, without limitation, slide arrays, silicon wafer arrays, liquid arrays, bead-based arrays and others described above in the definitions section or set forth in further detail below.

An array of arrays, also referred to as a composite array, having a plurality of individual arrays that is configured to allow processing of multiple samples can be used. Exemplary composite arrays that can be used in the invention are described in U.S. Pat. No. 6,429,027 and US 2002/0102578 and include, for example, one component systems in which each array is located in a well of a multi-well plate or two component systems in which a first component has several separate arrays configured to be dipped simultaneously into the wells of a second component. A substrate of a composite array can include a plurality of individual array locations, each having a plurality of probes and each physically separated from other assay locations on the same substrate such that a fluid contacting one array location is prevented from contacting another array location. Each array location can have a plurality of different probe molecules that are directly attached to the substrate or that are attached to the substrate via rigid particles in wells (also referred to herein as beads in wells). One or more assay locations of a composite array can include a stabilization polymer layer. Thus, a stabilization polymer layer can be uniformly distributed over a substrate, for example, covering several array locations of a composite array, or a stabilization polymer layer can be heterogeneously distributed over a substrate covering some portions and being absent in other portions.

In a particular embodiment, an array substrate can be fiber optical bundle or array of bundles, such as those generally described in U.S. Pat. Nos. 6,023,540, 6,200,737 and 6,327,410; and PCT publications WO9840726, WO9918434 and WO9850782. An optical fiber bundle or array of bundles can have probes attached directly to the fibers or via beads. Other substrates having probes attached to a substrate via beads are described, for example, in US 2002/0102578. A substrate, such as a fiber or silicon chip, can be modified to form discrete sites or wells such that only a single bead is associated with the site or well. For example, when the substrate is a fiber optic bundle, wells can be made in a terminal or distal end of individual fibers by etching, with respect to the cladding, such that small wells or depressions are formed at one end of the fibers. Beads can be non-covalently associated in wells of a substrate or, if desired, wells can be chemically functionalized for covalent binding of beads. Other discrete sites can also be used for attachment of particles including, for example, patterns of adhesive or covalent linkers. Thus, an array substrate can have an array of particles each attached to a patterned surface.

In some embodiments, beads can be attached to wells via a film forming polymer. A film forming polymer is a polymer that increase bead retention in wells compared to retention when the film forming polymer is absent. A film forming polymer can act as an adhesive between the wells and beads. Alternatively or additionally, a film forming polymer can coat a bead such that it is retained in a well. Exemplary film forming polymers include, without limitation, acrylamide or copolymers with C1-C12, aromatic and hydroxyl derivatives; acrylate copolymers; vinylpyrrolidine and vinylpyrrolidone copolymers; sugar based polymers such as starch or polydextrins; or other polymers such as polyacrylic acid, polyethylene glycol, polylactic acid, silicone, siloxanes, polyethyleneamines, guar gum, carrageenan, alginate, lotus bean gum, methacrylate co polymers.

Accordingly, the invention provides a method of attaching a bead to a well. The method can include the steps of contacting a well in a substrate with a film forming polymer; and contacting a bead to the well. The bead can be contacted with the well before, after or simultaneously with the film forming polymer.

A film forming polymer can be applied with a carrier solvent, such as a solvent disclosed herein with regard to applying a stabilization polymer. In particular embodiments, a film forming polymer is carried in dimethyl formamide or other suitable organic solvent. A method of attaching a bead to a well can include a step of allowing a film polymer to dry prior to contacting a polymer coated well with a bead. The time and conditions for drying can be selected to allow substantially all of the free carrier solvent to evolve. However, if desired partial drying can be carried out, for example, to favor bead retention due to tackiness or stickiness of a partially dried film forming polymer.

It will be understood that in some embodiments a polymer used in the invention can function as both a film forming polymer and a stabilization polymer. In other embodiments, the film forming polymer used for attaching a bead to a wells is different from a polymer used as a stabilization polymer layer. Accordingly, a method of the invention can include contacting a substrate with a first and second polymer, wherein the first and second polymers are different. The different polymers can be, for example, a film forming polymer and a stabilization polymer.

In a particular embodiment, a surface of a substrate can include physical alterations to attach probes or produce array locations. For example, the surface of a substrate can be modified to contain chemically modified sites that are useful for attaching, either-covalently or non-covalently, probe molecules or particles having attached probe molecules. Surface modifications can also be useful for improving attachment of a film forming polymer or stabilization polymer layer. Chemically modified sites can include, but are not limited to the linkers and reactive groups set forth above. Alternatively, polymeric probes can be attached by sequential addition of monomeric units to synthesize the polymeric probes in situ. Probes can be attached using any of a variety of methods known in the art including, but not limited to, an ink-jet printing method as described, for example, in U.S. Pat. No. 5,981,733; 6,001,309; 6,221,653; 6,232,072 or 6,458,583; a spotting technique such as one described in U.S. Pat. No. 6,110,426; a photolithographic synthesis method such as one described in U.S. Pat. No. 6,379,895 or 5,856,101; or printing method utilizing a mask as described in U.S. Pat. No. 6,667,394.

The size of an array used in the invention can vary depending on the probe composition and desired use of the array. Arrays containing from about 2 different probes to many millions can be made. Generally, an array can have from two to as many as a billion or more probes per square centimeter. Very high density arrays are useful in the invention including, for example, those having from about 10,000,000 probes/cm$^2$ to about 2,000,000,000 probes/cm$^2$ or from about 100,000,000 probes/cm$^2$ to about 1,000,000,000 probes/cm$^2$. High density arrays can also be used including, for example, those in the range from about 100,000 probes/cm$^2$ to about 10,000,000 probes/cm$^2$ or about 1,000,000 probes/cm$^2$ to about 5,000,000 probes/cm$^2$. Moderate density arrays useful in the invention can range from about 10,000 probes/cm$^2$ to about 100,000 probes/cm$^2$, or from about 20,000 probes/cm$^2$ to about 50,000 probes/cm$^2$. Low density arrays are generally less than 10,000 probes/cm$^2$ with from about 1,000 probes/cm$^2$ to about 5,000 probes/cm$^2$ being useful in particular embodiments. Very low density arrays having less than 1,000 probes/cm$^2$, from about 10 probes/cm$^2$ to about 1000 probes/cm$^2$, or from about 100 probes/cm$^2$ to about 500 probes/cm$^2$ are also useful in some applications.

An array or other substrate having one or more attached probes can have a stabilization polymer layer in the presence or absence of an optically detectable label. In particular embodiments, a stabilization polymer layer can function to protect a label from losing signal generating properties. However, a stabilization polymer layer need not function to protect an optical label. Rather, the layer can function to protect a probe molecule or target analyte from degradation including, for example, degradation that does not normally affect ability of the molecule to produce an optical signal. Thus, a substrate having a stabilization polymer layer can lack a label molecule, for example, during one or more steps of a method disclosed herein. In such embodiments, the label molecule can be added to the substrate after a period of storage or at a later stage of the method.

The invention further provides a method of making a probe composition. The method includes the steps of (a) providing a substrate having an attached biopolymer probe; and (b) contacting the substrate with a stabilization polymer.

A method of making a probe composition can be carried out by contacting a stabilization polymer with one or more of the substrates or probe compositions described previously herein. Contact can occur by bringing the substrate into contact with a stabilization polymer liquid, for example, by dipping the substrate into the stabilization polymer liquid. Alternatively, contact can occur by delivering a stabilization polymer liquid to the substrate, for example, by spotting, pipetting, painting on with a brush, vapor deposition, spraying, or using stimulus sensitive capsules that burst to release liquid under defined conditions such as changes in temperature, pressure or pH. Contact can be carried out under conditions that allow formation of a stabilization polymer layer. For example, liquid can be delivered as an aerosol that will evenly coat the substrate.

If desired, a further step of evenly distributing a stabilization polymer liquid on a substrate can be carried out following contacting the liquid and substrate. For example, spin coating can be used in which a stabilization polymer liquid is delivered to the surface of the substrate and the substrate is spun about an axis of rotation transecting the surface thereby causing the liquid to spread by centrifugal force. Alternatively, once the liquid is dispensed to the surface, the substrate can be centrifuged such that the surface faces an axis of rotation and orbits about the axis such that the liquid is spread across the surface. Other forms of agitation can also be used to spread a stabilization polymer liquid to form a layer including, for example, vortexing or shaking. Furthermore, a substrate to that is contacted with stabilization polymer in a method of the invention need not be agitated to distribute the stabilization polymer. Rather a layer can be formed by dispersion or flow of a stabilization polymer on a substrate.

In particular embodiments, a stabilization polymer liquid can include a carrier solvent. A carrier solvent and stabilization polymer can form a solution in which the polymer is dissolved in the solvent. A non-limiting advantage of using a solution is that the stabilization polymer will be homogeneously distributed throughout the liquid and can be evenly dispensed to a surface without requirements for agitating the liquid. However, a stabilization polymer liquid in which the polymer and carrier solvent form a mixture can also be used in the methods. A mixture can be stable to sedimentation such that substantial settling does not occur during distribution. If desired, a mixture can be agitated prior to dispensing or during dispensing, such that the stabilization polymer is evenly distributed on a surface. Furthermore, stabilization polymers that have favorable viscosity and liquid properties can be contacted to a substrate without the use of a carrier solvent if desired, Once a stabilization polymer liquid has been contacted with a surface, a carrier solvent, if present, can be removed. Removal of a carrier solvent can be partial. For example, in embodiments wherein an aqueous carrier solvent is used some of the water can be retained. For example, conditions for water removal can be such that substantially all of the free water is removed and bound water is retained. In particular embodiments, a carrier solvent is volatile such that it can be removed by evaporation. For example, polyacrylamide can be carried in water or a volatile alcohol solvent, and the solvent can be removed by drying in a 37° C. oven or in a dry box having an absorbent such as silica gel or Dri-Rite™ (Dri-Rite Company, Blue Island, Ill.). Drying can also be carried out under reduced pressure supplied, for example, by application of a vacuum pump. A carrier solvent can also be removed, for example, by washing. For example, following contact of a stabilization polymer liquid with a substrate bound probe the carrier solvent can be removed by washing with a second solvent that is compatible with the probe or a particular assay employing the probe. Typically, the washing solvent is one that will not dissolve the stabilization polymer layer.

In particular embodiments, a carrier solvent used for delivery of a stabilization polymer to a substrate bound probe can be compatible with conditions for use of the probe such that the solvent need not be removed prior to use of the probe. For example, water can be used to carry a stabilization polymer for coating an array of biopolymer probes. Because water is compatible with most applications of biopolymer arrays the array can be used without removing the water. Those skilled in the art will know or be able to routinely determine a carrier solvent that is compatible with a particular stabilization polymer or, if desired, that can be removed following polymer delivery to a substrate based on known properties of the polymer and/or solvent. Exemplary methods are demonstrated in Examples I and II.

A stabilization polymer layer can be added to a substrate at any of a variety of stages of solid-phase probe manufacture. In particular embodiments, a stabilization polymer layer can be added to a substrate having one or more probes attached thereto. Alternatively, a substrate can have a stabilization polymer layer prior to attachment of one or more probes. The type of polymer and reaction conditions used can be selected for compatibility as set forth above. For example, the polymer can be chosen for ability to be retained under conditions used for probe attachment, synthesis, and/or binding to target. It is also contemplated to add a stabilization polymer to a component of a substrate prior to assembling with a second component. For example, in the case of arrays that use particles attached to a second substrate, such as a bead in well format, a stabilization polymer layer can be added to the particles prior to assembly with the second substrate. Accordingly, a stabilization polymer layer can have the added property of assisting in adherence of the particles to the second substrate as set forth herein previously. However, in other embodiments the stabilization polymer layer is not an adhesive or does not form a bond or attachment between two substrates such as a bead and a well. Methods for loading beads and other particles onto array substrates that can be used in the invention are described, for example, in U.S. Pat. No. 6,355,431 and/or as described above with regard to film forming polymers.

In some embodiments, for example when chemical attachment is done, probes or particles with associated probes can be attached to a substrate in a non-random or ordered process. For example, using photoactivatable attachment linkers or photoactivatable adhesives or masks, selected sites on an array substrate can be sequentially activated for attachment, such that defined populations of probes or particles are laid down at defined positions when exposed to the activated array substrate.

Alternatively, probes or particles with associated probes can be randomly deposited on a substrate and their positions in the array determined by a decoding step. This can be done before, during or after the use of the array to detect target molecules. In embodiments where the placement of probes is random, a coding or decoding system can be used to localize and/or identify the probes at each location in the array. This can be done in any of a variety of ways, as is described, for example, in U.S. Pat. No. 6,355,431.

The invention provides a method of detecting a target analyte. The method includes the steps of (a) providing a substrate having an attached probe molecule, and further having a stabilization polymer layer; (b) contacting the substrate with a target analyte, wherein the target analyte specifically binds to the attached probe molecule; and (c) detecting the presence of the target analyte.

A target analyte can be contacted with a probe molecule; such as a biopolymer probe, under conditions that allow binding to occur between the target analyte and probe molecule. Typically, conditions used in the methods favor selective binding of probe molecules to target analytes compared to binding of the probe to non-target analytes in a test sample. Accordingly, a probe molecule can bind to a target analyte under the conditions of the methods with a dissociation constant that is, for example, less than about $10^{-4}$, $10^{-5}$, $10^{-6}$, $10^{-7}$, $10^{-8}$, $10^{-9}$ $10^{-10}$, $10^{-11}$, or $10^{-12}$ M$^{-1}$. Those skilled in the art will know or be able to determine appropriate conditions for binding a particular probe molecule and target analyte pair or population of probe-analyte pairs. In accordance with the methods and compositions disclosed herein, a probe molecule can selectively bind a target analyte in the presence of a stabilization polymer layer.

Binding of a target analyte to a substrate-attached probe molecule can be detected due to a change in signal localized at or near the substrate-attached probe. Such changes can include, for example, an increase in signal due to the binding of a labeled target analyte, an increase in signal due to modification of a probe, target or both to incorporate a label when bound to each other, or decrease in signal due to modification of a probe, target or both to remove or quench a label when bound to each other.

In embodiments in which a target polynucleotide is contacted with a probe polynucleotide, detection can be based on the presence of a labeled target polynucleotide hybridized to a substrate bound probe polynucleotide. For example, a pre-labeled polynucleotide fragment having a particular single nucleotide polymorphism (SNP) can be identified based on presence of the label at a particular array location where a polynucleotide complementing the SNP resides. A method of the invention can be used for a variety of analyses including, but not limited to, genotyping, gene expression analysis, sequencing, mutation detection or other genetic determinations.

In some embodiments, a substrate attached to a polynucleotide probe can be modified while hybridized to a target polynucleotide, thereby allowing detection. Such embodiments include, for example, those utilizing allele-specific primer extension (ASPE), single base extension (SBE), oligonucleotide ligation amplification (OLA), rolling circle amplification (RCA), extension ligation (GoldenGate™), invader technology, probe cleavage or pyrosequencing as described in U.S. Pat. No. 6,355,431 B1 or U.S. Ser. No. 10/177,727. Thus, the invention can be carried out in a mode wherein an immobilized polynucleotide probe is modified instead of a target polynucleotide captured by a probe. Alternatively, detection can include modification of the target nucleic acid while hybridized to probes. Exemplary modifications include those that are catalyzed by an enzyme such as a polymerase. A useful modification can be incorporation of one or more nucleotides or nucleotide analogs to a primer hybridized to a template strand, wherein the primer can be either the probe or target in a probe-target hybrid. Such a modification can include replication of all or part of a primed template.

A method of the invention can include a step of detecting an optical signal from a target analyte or a probe molecule. Exemplary optical signals include, without limitation, a fluorescent signal, absorption signal, luminescent signal, chemiluminescent signal or the like. Detectable signal changes can arise due to an intrinsic property of a target analyte, probe molecule or probe-target complex. Alternatively or additionally, a detectable signal change can arise due to the presence or absence of an extrinsic label or quencher associated with a target analyte, probe molecule or both. Other types of signals can also be detected in a method of the invention including, for example, those arising from labels described below.

A label can be a primary label that is directly detectable or secondary label that can be indirectly detected, for example, via direct or indirect interaction with a primary label. Exemplary primary labels include, without limitation, an isotopic label such as a naturally non-abundant radioactive or heavy isotope; chromophore; luminophore; fluorophore; calorimetric agent; magnetic substance; electron-rich material such as a metal; electrochemiluminescent label such as Ru(bpy)32+; or moiety that can be detected based on a nuclear magnetic, paramagnetic, electrical, charge to mass, or thermal characteristic. Fluorophores that are useful in the invention include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue, Texas Red, alexa dyes, phycoerythin, bodipy, and others known in the art such as those described in Haugland, *Molecular Probes Handbook*, (Eugene, Oreg.) 6th Edition; *The Synthegen catalog* (Houston, Tex.), Lakowicz, *Principles of Fluorescence Spectroscopy*, 2nd Ed., Plenum Press New York (1999), or WO 98/59066. Labels can also include enzymes such as horseradish peroxidase or alkaline phosphatase or particles such as magnetic particles or optically encoded nanoparticles. Typically, a stabilization polymer layer is transparent in the wavelength region used for detection of an optical label. However, it is also possible to remove a stabilization polymer layer prior to a detection step if desired.

A secondary label can be a binding moiety attached to a target or probe to allow detection via specific affinity for a receptor. Exemplary pairs of binding moieties and receptors that can be used in the invention include, without limitation, antigen and immunoglobulin or active fragments thereof, such as FAbs; immunoglobulin and immunoglobulin (or active fragments, respectively); avidin and biotin, or analogs thereof having specificity for avidin such as imino-biotin; streptavidin and biotin, or analogs thereof having specificity for streptavidin; carbohydrates and lectins; and other known proteins and their ligands. Binding of a secondary label to a partner binding moiety can occur in the presence or absence of a stabilization polymer layer. Those skilled in the art will know or be able to determine compatible binding moieties and polymer layers based on known properties of the moieties and polymers.

The invention is particularly useful for probe arrays. Thus, a composition or method disclosed herein can include a plurality of probe molecules attached to a substrate, for example, on an array as set forth above. Accordingly, a method of the invention can include a step of contacting an array substrate with a plurality of target analytes wherein the target analytes bind to a plurality of probes attached to the array. One or more target analytes can be contacted with an array in the presence of a stabilization polymer layer. Typically, the layer will not substantially prevent binding between probe and target.

In particular embodiments a stabilization polymer layer can be removed prior to contacting a target analyte with a substrate having an attached probe molecule. A stabilization polymer can be removed by washing in a solvent in which the polymer is soluble, such as a carrier solvent as described previously herein. For example, a polyacrylamide layer can be removed by washing in water or an aqueous buffer.

An advantage of the invention is that a stabilization polymer allows a substrate bound probe or array of probes to be stored for an extended period of time. Accordingly, a method of the invention can include a step of placing the substrate in a storage location prior to contacting it with a target analyte. A substrate having a stabilization polymer layer can be stored for a period of time including, for example, at least 24, 48, 36, 72 or more hours. The temperature for storage can be any that is compatible with the substrate, probe and stabilization polymer being used. For example, an array of biological probes having a stabilization polymer layer of the invention can be stored at a temperature in the range of −20° C. to 45° C. Humidity also can be selected for compatibility with substrate, probe and polymer and can include, for example, a humidity in the range of 5% to 95%. Extended storage can be, for example, at least 4 days, 1 week, 1 month or 6 months. Storage can occur under ambient conditions such as those of a typical laboratory.

Alternatively a substrate having a stabilization polymer layer can be placed in a package. The package can be a sealed container, thereby substantially preventing transfer of gases into and out of the container. Exemplary containers include, without limitation, a polyethylene terephthalate copolyester (PETG) container, metalized bag, glass or plastic Petri dish, or plastic bag such as a Ziplock™ bag. Packaging can further include a desiccant, inert gas or can be vacuum evacuated.

A further advantage of the invention is that a stabilization polymer allows a substrate bound probe or array of probes to be shipped between remote locations. Accordingly, the invention provides a method of shipping a solid-phase probe. The method includes the steps of (a) providing a substrate having an attached probe molecule, and further having a stabilization polymer layer; (b) placing the substrate in a package; and (c) shipping the package to a remote location.

A method of the invention can include a step of obtaining a package containing a substrate having an attached probe, and further having a stabilization polymer layer. The package can be obtained from a local or remote location.

A further advantage of the invention is that use of a stabilization polymer layer can facilitate reuse of a substrate-attached probe molecule. Thus, a method of detecting a target analyte can include the steps of (a) providing a substrate having an attached probe molecule; (b) contacting the substrate with a first target analyte wherein the first target analyte specifically binds to the attached probe molecule; (c) detecting the presence of the first target analyte; (d) removing the first target analyte; (e) contacting the substrate with a stabilization polymer; (f) contacting the substrate with a second target analyte wherein the second target analyte specifically binds to the attached probe molecule; and (g) detecting the presence of the second target analyte. The substrate provided in step (a) can include a stabilization polymer layer if desired. Furthermore, the method can include a step of placing the substrate in a storage location after step (e) and prior to step (f). Storage can be carried out, for example, as set forth above.

Use of a stabilization polymer layer can allow a solid-phase probe to be reused numerous times. Thus, a method of the invention can be repeated, for example, at least 1, 2, 3 or more times. Furthermore, a stabilization polymer layer allows a portion of the arrays present in an array of arrays to be protected from degradation while other sections are used. For example, 8 arrays from an array of 96 arrays can be used in an analytical method at a first time while the unused arrays (88 in this case) are protected from adverse ambient conditions encountered during manipulation and storage of the array. Then at a second, later time all or a portion of the unused arrays can be used in a second analytical method.

The following examples are intended to illustrate but not limit the present invention.

Example I

Stabilization of BeadChip Arrays by a Polyacrylamide Layer

This example demonstrates a stabilization effect due to a layer of polyacrylamide on surface attached nucleic acid probes. In particular, stabilization of BeadChip Arrays is demonstrated.

Human Tox BeadChip Arrays were obtained from Illumina, Inc. (San Diego). BeadChip Arrays are silicon chips having several arrays of attached beads, each bead being coated with a different nucleic acid probe. In the case of the Human Tox version, the probes are complementary to target gene transcripts that are differentially expressed in human cells in response to toxins. Also included on the Human Tox BeadChip Arrays are probes to various housekeeping genes whose expression is constant under a variety of conditions.

Five Human Tox BeadChip Arrays were placed on a laboratory bench top under typical ambient conditions for 0, 1, 2, 3 and 8 hours, respectively. Each Beadchip Array was then hybridized to a sample of biotin labeled copy RNA (cRNA). The cRNA was produced by reverse transcription of an RNA sample to produce cDNA having poly T tails, followed by amplification with polymerase with poly A primer and in vitro transcription incorporating biotinylated dUTP. The cRNA sample was hybridized to the array overnight at 55° C. with mixing. Unbound target molecules were washed away and hybridized. Biotinylated targets were incubated with Cy3 labeled streptavidin. BeadChip Arrays were then detected using an Axon scanner (Axon Instruments) at 635 nm to detect the Cy3 label.

As shown in FIG. 1, exposure of arrays to ambient conditions for 2, 3 and 8 hours led to a drop in signal intensity of 31%, 53% and 75%, respectively when expression of housekeeping genes was measured.

Figure 2:
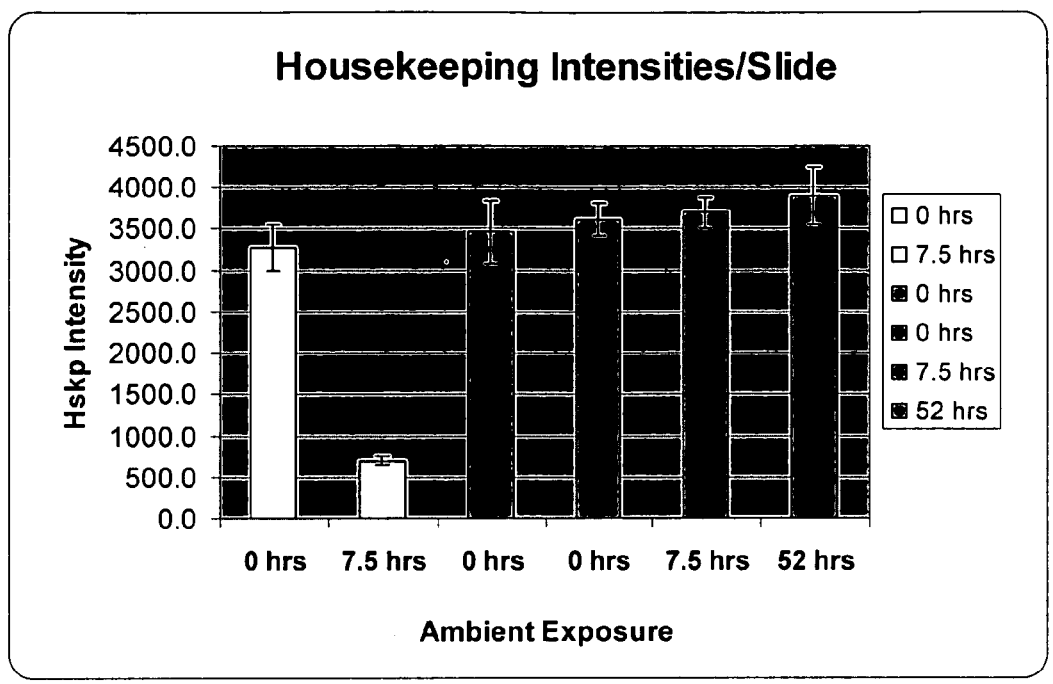
FIG. 2 shows signal intensity for BeadChip Arrays that were coated with polyacrylamide when exposed to ambient conditions prior to hybridization and detection (shaded bars) or that were not treated with polyacrylamide after exposure to the same ambient conditions prior to hybridization and detection (white bars).

To a separate set of BeadChip Arrays was pipetted polyacrylamide having an estimated molecular weight of about 10 kDa, followed by drying on a 37° C. heat block for 30 minutes. The BeadChip Arrays were placed on a laboratory bench top under typical ambient conditions for 0, 7.5 and 52 hours, respectively. Each BeadChip Array was then hybridized and detected as described above. As shown in FIG. 2, BeadChip Arrays that were coated with polyacrylamide showed no significant decrease in signal intensity when exposed to ambient conditions for over 52 hours prior to hybridization and detection (shaded bars). In contrast, control BeadChip Arrays that were not treated with polyacrylamide experienced a 79% decrease in signal after exposure to the same ambient conditions for only 7.5 hours prior to hybridization and detection (white bars). Similar experiments showed that BeadChip Arrays that were coated with polyacrylamide experienced no significant loss in signal to noise when incubated at 45° C. in a sealed package for up to 26 days prior to hybridization and detection.

Example II

Stabilization of Fiber Optic Bead Arrays by a Polyacrylamide Layer

This example demonstrates a stabilization effect due to a layer of polyacrylamide on nucleic acid probes attached to fiber optic based bead arrays.

An array of 96 fiber optic bundles, each bundle being an array of etched fibers, and each fiber having an attached bead (Sentrix® BeadArray™, Illumina Inc., San Diego) was treated as follows. In order to demonstrate the extent of degradation for untreated fiber optic arrays, array bundles were placed on a benchtop and exposed to ambient laboratory conditions for varying times (1, 2, 4, 6, 8 and 16 hours) prior to hybridization and detection. Arrays were preconditioned with NaOH, phosphate buffer, and formamide as recommended by the manufacturer.

Sentrix® BeadArrays™ are randomly loaded with beads having attached "illumicode" nucleotide sequences. The location of beads on the array can be subsequently determined using dye labeled decoder probes prior to carrying out the stability analysis. For the present stability analysis a subset of decoder probes labeled with Cy3 was hybridized to the arrays. Hybridization was carried out for 12 minutes at room temperature. Sentrix® BeadArrays™ were then detected using a BeadArray™ scanner (Illumina, Inc., San Diego).

The results of the hybridization study showed that degradation occurred similar to that observed on BeadChip arrays with about 80% signal loss after 16 hours.

In order to demonstrate the stabilizing properties of polyacrylamide on Sentrix® BeadArrays™ different bundles (individual arrays) on the same array of arrays were each respectively coated with: (1) no polymer layer (untreated); (2) a polyacrylamide layer, added to arrays as a 2% mixture in water according to the methods described in Example 1; (3) a HEPES/TRIS buffer.

Specific bundles on the BeadArray™ were preconditioned each night over a 8 night period. The bundles were hybridized to Cy3 labeled decoder probes at a 20 pM concentration over night in a temperature ramp consisting of a 40 min hold at 60° C. then 1° C. decrease every 30 min to 45° C. where temp was held until array removal for washing. The BeadArray™ was imaged dry using a BeadArray™ scanner as described above.

Bundles that were not coated with a stabilization polymer (untreated) experienced a 77% loss of signal intensity after 7 hybridization cycles. In contrast, bundles that were coated with polyacrylamide showed only a 47% decrease. Bundles treated with HEPES/TRIS buffer were slightly more stable than untreated bundles (59% decrease in signal intensity) but less stable than polyacrylamide coated bundles.

In addition to the decrease in intensity it was noted that by day 3 the histograms for untreated bundles were not well separated, indicating that the data was of poor quality for typical genetic analysis. The histograms of HEPES/TRIS buffer treated bundles were poorly separated after 5 days. However, histograms for bundles that were coated with polyacrylamide were well separated up to and including day 8.

Example III

Stabilizing Effects of Polymers for a Variety of Array Platforms and Assay Methods This Example demonstrates stabilizing effects of polyvinylpyrrolidone and polyacrylamide on fiber optic-based arrays (Sentrix® BeadArrays™) and silicon chip-based arrays (BeadChip Arrays) when used in conjunction with genotyping and gene expression assays.

Sentrix® BeadArrays™ and BeadChip Arrays (Illumina, Inc., San Diego) were coated with Supermount (Biogenex Laboratories, San Ramon, Calif.), coated with polyacrylamide or untreated. Supermount is an aqueous mixture of polyvinylpyrrolidone (PVP). Arrays were coated with Supermount or 2% polyacrylamide in water as set forth in Examples I and II. Arrays were then stored in one of the three following conditions: (1) on a laboratory benchtop under ambient conditions for 8 hours; (2) in a PETG box (referred to as the "clam shell." Note the clam shell is not airtight) for 8 hours; or (3) in a sealed package for 8 hours (this condition is referred to as T=0). The sealed package was a PETG box enclosed in a heat sealed metalized bag that had been evacuated by vacuum followed by backfilling with nitrogen and included a desiccant pouch.

A low concentration foreground (LCFG) assay was carried out on Sentrix® BeadArrays™ or BeadChip Arrays under typical genotyping assay conditions. The conditions were similar to genotyping assay conditions with the exception that decoder probes labeled with Cy3 were used in place of GoldenGate™ probes normally amplified from genomic DNA. Arrays were preconditioned as set forth above in Examples I and II. Decoder probes labeled with Cy3 at 20 pM were hybridized to preconditioned Sentrix® BeadArrays™ as described in Example II. Hybridization solutions were those used in the GoldenGate™ genotyping assays (Illumina, Inc., San Diego). Sentrix® BeadArrays™ were detected using a BeadArray™ scanner and BeadChip Arrays were detected using an Axon scanner.

Gene Expression (GEx) assays were carried out on Sentrix® BeadArrays™ or BeadChip Arrays under conditions described in Example I. Sentrix® BeadArrays™ were preconditioned as set forth above in Example I and BeadChip arrays were not preconditioned. Hybridization was carried out for 16-18 hours at 55° C. Sentrix®BeadArrays™ were detected using a BeadArray™ scanner and BeadChip Arrays were detected using an Axon scanner.

As shown in Table 1, for LCFG assays run under genotyping conditions, percent loss of signal intensities detected on BeadChip sections treated with supermount or polyacrylamide was significantly lower compared to signal loss detected on untreated sections. More specifically, for BeadChip Arrays that were exposed to ambient conditions, untreated arrays experienced a 30 fold increase in signal loss compared to polyacrylamide coated arrays and a 12 fold increase in signal loss compared to supermount treated arrays. Although some protection was afforded by storage in a clam shell, untreated arrays still experienced a 23 fold increase in signal loss compared to polyacrylamide coated arrays and a 3 fold increase in signal loss compared to supermount coated arrays.

TABLE 1

LCFG on BeadChip Arrays

| treatment | Clam shell (% intensity loss relative to T = 0) | Benchtop (% intensity loss relative to T = 0) |
|---|---|---|
| untreated | 28.0 | 62.7 |
| polyacrylamide | 1.21 | 2.16 |
| supermount | 8.53 | 5.38 |

As shown in Table 2, only small differences in genotyping signal intensity loss were observed for Sentrix® BeadArray™ fiber bundles stored in the clam shell. However, for fiber bundles stored under ambient conditions on a laboratory benchtop, untreated fibers experienced a 4 fold increase in signal loss compared to polyacrylamide coated arrays and a 7 fold increase in signal loss compared to supermount coated arrays.

TABLE 2

LCFG on Sentrix ® BeadArrays ™

| treatment | Clam shell (% intensity loss relative to T = 0) | Benchtop (% intensity loss relative to T = 0) |
|---|---|---|
| untreated | −1.07 | 20.8 |
| polyacrylamide | −5.82 | 5.33 |
| supermount | −3.01 | 2.84 |

As shown in Table 3, loss of gene expression signal intensity for BeadChips stored in the clam shell was comparable for untreated, polyacrylamide coated and supermount coated bundles. However, when stored under ambient conditions, untreated fibers experienced increased gene expression signal loss compared to polyacrylamide coated arrays and supermount coated arrays

TABLE 3

GEx on BeadChip Arrays

| treatment | Cy3 Med (% intensity loss relative to T = 0) | Cy3 High (% intensity loss relative to T = 0) | Housekeeping (% intensity loss relative to T = 0) |
|---|---|---|---|
| Clam shell | | | |
| Untreated | 51.6 | 37.0 | 18.0 |
| Polyacrylamide | 50.5 | 34.4 | 11.6 |
| Supermount | 54.4 | 38.7 | 21.9 |
| Benchtop | | | |
| Untreated | 92.9 | 92.4 | 67.0 |
| Polyacrylamide | 75.8 | 58.0 | 26.6 |
| Supermount | 77.2 | 60.8 | 34.5 |

In a further analysis, GEx assays were carried out on BeadChip Arrays that were untreated, coated with polyacrylamide or coated with supermount. The arrays were stored on the benchtop under ambient conditions for 0 or 8 hours and then subjected to hybridization and detection. The results were compared to Sentrix® BeadArrays™ that were treated similarly with the exception that the bundles were washed with water to remove the coating after storage and prior to hybridization and detection (whereas BeadChip arrays were not washed). Housekeeping intensities were similar for washed and non-washed slides. Generally, background intensity was slightly higher for non-washed slides and signal to noise was higher for washed slides. However, performance of the GEx assay in the presence of the polymer layers or following removal of the polymer layers was not adversely affected in the conditions tested.

These results indicate that a variety of stabilization polymer layers can protect several different array platforms from loss of signal intensity when used for a variety of assays. Furthermore, presence of a stabilization polymer layer does not adversely affect efficiency for various assays on various assay platforms.

Example IV

Evaluation of Stabilization Polymer Delivery Methods on Stability of Fiber Optic Bead Arrays This example demonstrates methods for varying carrier solvent properties for delivery of polyacrylamide to a fiber optic-based array substrate and methods for evaluating the resulting stabilization polymer layer.

Fiber optic bundles of Sentrix® BeadArrays™ were treated, individually, with the following mixtures: 2% polyacrylamide in water; 2% polyacrylamide (PA) in water spiked with 10 to 50% ethanol; 2% PA in water spiked with 10 to 50% methanol; 2% PA in salt where salt was selected from 2 mM or 2M NaCl in water, 2 mM or 2M KCl in water, or 2 mM or 2M $CaCl_2$ in water; or 2% polymer in water where polymer was selected from 25% PA: 75% polyethylene glycol (PEG) 9 kDa, 50% PA: 50% PEG 9 kDa, 75% PA: 75% PEG 9 kDa, 25% PA: 75% PEG 0.8 kDa, 50% PA: 50% PEG 0.8 kDa, 75% PA: 75% PEG 0.8 kDa, 25% PA: 75% polyacrylic acid (PAAc), 50% PA: 50% PAAc, or 75% PA: 75% PAAc. Also tested was treatment with mixtures containing 2% polyacrylamide in water containing Magnesium chloride, magnesium acetate, acetone, dimethylsulfoxide (DMSO) or glycol. Treatment was carried out by dipping replicate bundles into each of the above mixtures, allowing the bundles to dry and storing the array of bundles for 3 days (first replicate under ambient conditions and second replicate at 45° C. in a clam shell).

Following storage, the arrays were hybridized and detected as described in Example I.

Histogram analysis of bead intensity vs. the number of beads scanned showed the following results. As the concentration of alcohol was increased in the carrier solvent, average bead intensity also increased. The observed intensity increase was more pronounced at the elevated temperature. As alcohol concentration increased a slight increase was observed in background fluorescence, a decrease in coefficient of variation (CV) was observed and an increase in signal to noise was observed.

For the salts tested, only $CaCl_2$ caused significant differences compared to water alone. $CaCl_2$ caused a decrease in signal intensity, an increase in CV and decrease in signal to noise and background fluorescence. The other salts when used in polyacrylamide carrier solvents had insignificant effects on probe stability.

For the polymers tested in combination with polyacrylamide, increasing PAAc was found to increase background while increasing PEG was found to decrease signal intensity.

When polyacrylamide was delivered in the presence of acetone, signal to noise increased and background fluorescence decreased. When polyacrylamide was delivered in the presence of DMSO, background fluorescence increased. When polyacrylamide was delivered in the presence of glycol, signal to noise increased.

Overall, addition of methanol or NaCl to polyacrylamide carrier solvent had beneficial effects on array stability at the elevated temperature.

Example V

Evaluation of Stabilization Polymer Delivery Methods on Stability of BeadChip Arrays This example demonstrates stabilization of BeadChip Arrays using polyacrylamide layers. This example further demonstrates the stability of BeadChip Arrays when polyacrylamide is delivered in carrier solvents having different compositions.

Replicate BeadChip Arrays were treated, individually, with the following mixtures: 2% PA in water; 2% PA in phosphate buffer; 2% PA in 50:50::water:methanol; and 2% PA in 3.66 mM NaCl (aqueous). All BeadChip Arrays were spotted with the above mixtures and dried on a heat block. The first replicate (referred to as T=0) for each pair was immediately packaged and stored in a drybox. The second replicate (referred to as T=5 days) was stored at 45° C. for 5 days. The BeadChips were then hybridized and detected as set forth in Example IV.

Figure 3:
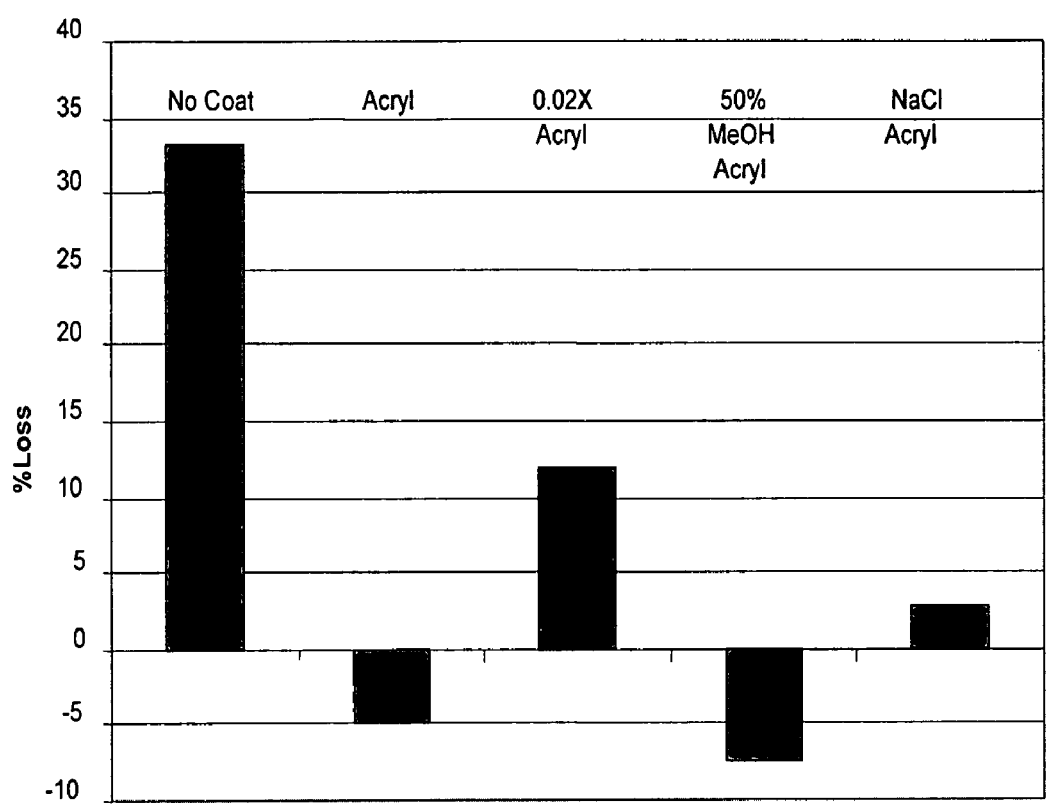
FIG. 3 shows signal intensity for BeadChip Arrays that were coated with polyacrylamide and BeadChip Arrays that were not coated with polyacrylamide after 5 days of storage.

As shown in FIG. 3, after 5 days BeadChip Arrays that were not coated with polyacrylamide showed the largest loss of intensity (over 30%). In contrast, BeadChips that were coated with polyacrylamide had up to 8 fold less signal loss. BeadChips coated with polyacrylamide delivered in water showed a 5% increase in signal after 5 days of storage and BeadChips coated with polyacrylamide delivered in 50:50::water:methanol showed a nearly 8% increase in signal after 5 days of storage.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of detecting a target analyte, comprising
   (a) providing a substrate comprising an attached polynucleotide, wherein the substrate further comprises a stabilization polymer layer;
   (b) storing said substrate for a period of at least 24 hours;
   (c) removing said stabilization polymer layer from said substrate;
   (d) contacting said substrate with a target analyte, wherein said target analyte specifically binds to said attached polynucleotide; and
   (e) detecting the presence of said target analyte.

2. The method of claim 1, further comprising placing said substrate in a storage location.

3. The method of claim 2, wherein said placing said substrate in a storage location further comprises placing said substrate in a package.

4. The method of claim 3, wherein said package comprises a sealed container.

5. The method of claim 1, wherein said providing in step (a) comprises obtaining a package comprising said substrate.

6. The method of claim 5, wherein said package is obtained from a remote location.

7. The method of claim 5, wherein said package comprises a sealed container.

8. The method of claim 1, wherein said target analyte comprises a polypeptide.

9. The method of claim 1, wherein step (c) comprises detecting an optical signal from said target analyte or said attached polynucleotide.

10. The method of claim 9, wherein said optical signal comprises a fluorescent signal.

11. The method of claim 1, wherein said substrate comprises an array of attached polynucleotides.

12. The method of claim 11, wherein step (b) comprises contacting said substrate with a plurality of target analytes, wherein target analytes bind to said array of attached polynucleotides.

13. The method of claim 1, 11 or 12, wherein the stabilization polymer layer comprises hyaluronic acid capable of retaining at least 75% weight of water compared to dry weight of the polymer.

14. The method of claim 1, 11 or 12, wherein the stabilization polymer layer comprises hyaluronic acid having an average molecular weight of 100 kDa.

15. The method of claim 1 or 12, wherein the stabilization polymer layer comprises polyethylene glycol.

16. The method of claim 1, wherein the stabilization polymer layer further comprises glycol.

17. The method of claim 1 or 12, wherein the stabilization polymer layer comprises polyvinylpyrrolidine.

18. The method of claim 1, wherein the stabilization polymer layer further comprises $CaCl_2$.

19. The method of claim 1, wherein the stabilization polymer layer further comprises methanol.

20. The method of claim 1, 11, 12, 18, 19 or 16, wherein the stabilization polymer layer comprises polyacrylamide.

21. The method of claim 1, 11 or 12, wherein the stabilization polymer comprises polyacrylic acid.

22. The method of claim 1, wherein the period in step (b) is at least 1 week.

23. The method of claim 1, wherein said target analyte comprises a polynucleotide.

24. The method of claim 1, 11, 12, 18, 19 or 16, wherein the stabilization polymer layer comprises hyaluronic acid.

* * * * *